United States Patent
Choi et al.

(10) Patent No.: US 6,577,706 B2
(45) Date of Patent: Jun. 10, 2003

(54) MEASUREMENT OF LATERAL YARN DENSITY DISTRIBUTION

(75) Inventors: Ka-fai Choi, Kowloon (HK); Yuen-wah Wong, Kowloon (HK)

(73) Assignee: The Hong Kong Polytechnic University, Kowloon (HK)

(*) Notice: Subject to any disclaimer, the term of this patent is extended or adjusted under 35 U.S.C. 154(b) by 0 days.

(21) Appl. No.: 09/921,271

(22) Filed: Aug. 3, 2001

(65) Prior Publication Data
US 2003/0068007 A1 Apr. 10, 2003

(51) Int. Cl.⁷ .............................. G01B 15/02
(52) U.S. Cl. ................ 378/54; 378/58; 378/61; 250/390.06
(58) Field of Search ................ 378/54, 58, 61; 250/390.04, 390.06

(56) References Cited

U.S. PATENT DOCUMENTS

| 5,255,302 A | * | 10/1993 | Shimamune et al. | ........ 378/207 |
| 5,277,928 A | * | 1/1994 | Strandberg | .................. 118/420 |
| 5,379,336 A | * | 1/1995 | Kramer et al. | ......... 250/370.09 |
| 5,748,705 A | * | 5/1998 | Stein et al. | .................. 378/196 |

\* cited by examiner

Primary Examiner—Robert H. Kim
Assistant Examiner—George Wang
(74) Attorney, Agent, or Firm—Leydig, Voit & Mayer, Ltd.

(57) ABSTRACT

An apparatus for measuring the lateral yarn density distribution of a yarn uses selected X-ray radiation. Radiation absorption is determined in a number of narrow planes across the yarn and in two or more rotational orientations. The measuring takes place without any damage to or physical interference with the yarn.

7 Claims, 3 Drawing Sheets

MEASUREMENT OF LATERAL YARN DENSITY DISTRIBUTION

BACKGROUND OF THE INVENTION

1. Field of the Invention

The invention relates to apparatus for measuring lateral yarn density distribution.

2. Description of Prior Art

During textile spinning processes, the fibre stream is arranged to form a yarn in many different ways according to the spinning method, machine setting and initial geometry of the fibres in the sliver or roving, This leads to a spun yarn with different structures and mechanical properties. A tracer fibre technique is an effective way to study the fibre path in a yarn. Together with an image analysis algorithm, a large number of tracer fibres can be sampled and a better representation of the yarn structure can be obtained. The yarn cross-section analysis provides some further information on the yarn structure, for example the fibre packing density distribution in a yarn. A very important yarn parameter is related to the highly non-linear torsional and tensile properties of yarn, and the initial lateral compression modulus of fabric and hence fabric handle.

A conventional method of fibre lateral distribution measurement is called the slice cutting method. The procedures of this method include fixing the yarn by means of resin and cutting thin slices of the fixed yarn. The fibres in the yarn cross-section can then be analysed manually or automatically by means of image analysis. The disadvantages of the slice cutting method are that, firstly the yarn structure may be changed in the resin bath, and, secondly, this method is a destructive test. As a result, the same portion of yarn cannot be used for other tests. The method is also tedious and time consuming to carry out.

SUMMARY OF THE INVENTION

It is an object of the invention to eliminate the short comings of the conventional method.

According to the invention there is provided a apparatus for measuring the lateral yarn density distribution of a yarn comprising a collimated source of radiation having a selected wavelength within the range of 0.04 nm to 0.25 nm (corresponding to a radiation energy of 30 KeV to 5 KeV), means for holding a length of yarn with a section thereof across a path of the radiation in different rotational orientations between the source and a radiation detector, and a computer programmed to determine the density distribution based on radiation absorption of the yarn in adjacent narrow planes at two or more orientations.

The collimated radiation may be constricted to a path extending over a narrow plane of the section of the yarn and the radiation detector arranged to respond to radiation present beyond the yarn along that narrow path, in which the means for holding the yarn is arranged to move the yarn in steps into different planes in the path of radiation.

The radiation preferably has a wavelength of 0.083 nm (corresponding to a radiation energy of 15 KeV) or 0.15 nm (corresponding to a radiation energy of 8 KeV).

The computer preferably uses a process for determining the yarn density relying on the principle of computed tomography (CT).

BRIEF DESCRIPTION OF THE DRAWINGS

Apparatus for measuring relative yarn density distribution according to the invention will now be described by way of example with reference to the accompanying drawings in which.

DESCRIPTION OF THE PREFERRED EMBODIMENT

Figure 1:
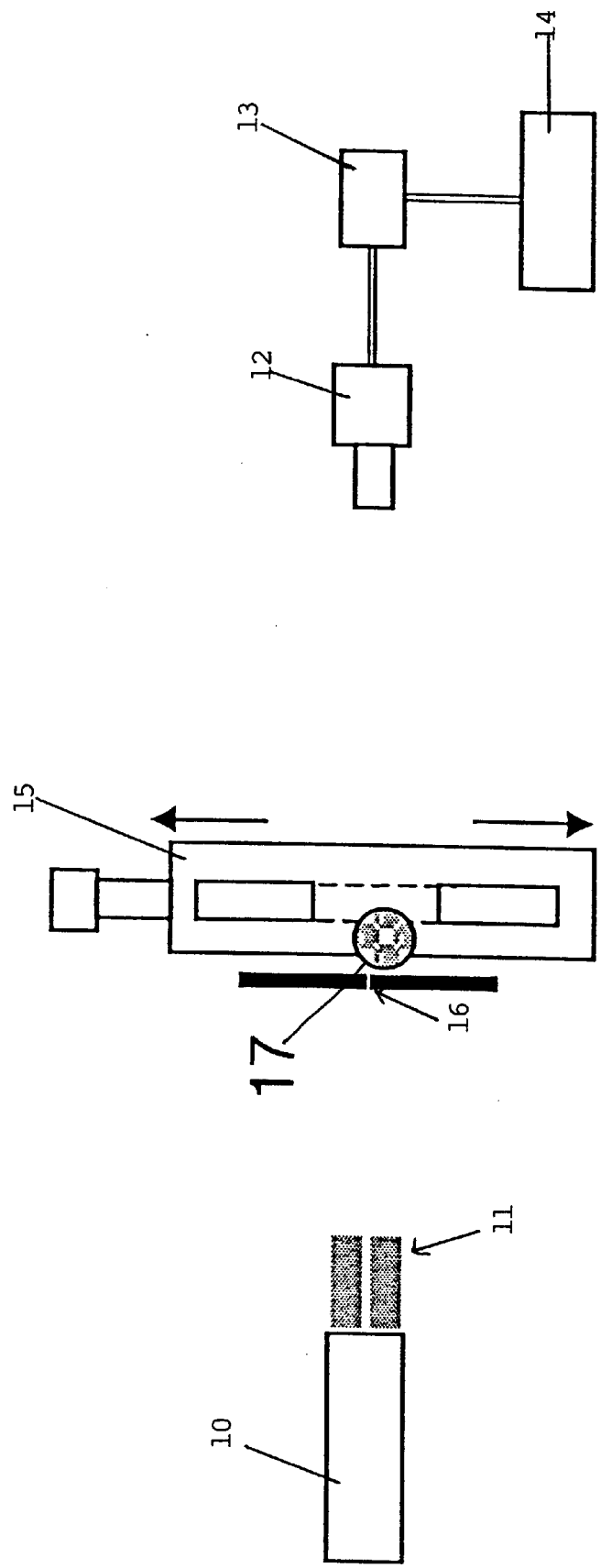
FIG. 1 is a schematic arrangement of the apparatus.
Figure 2:
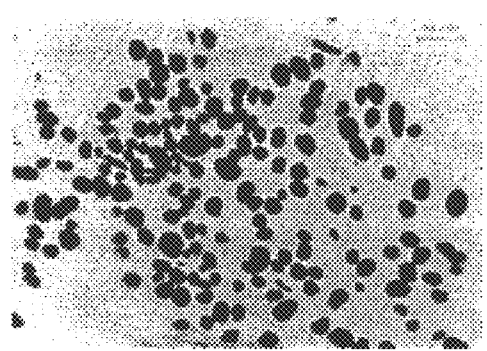
FIG. 2 is a typical cross-sectional view of a cross-section of yarn having a low twist.
Figure 3:
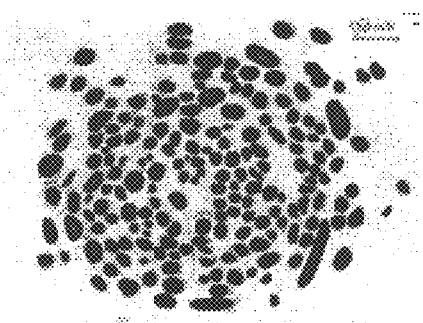
FIG. 3 is a typical cross-sectional view of yarn having a high twist.
Figure 4:
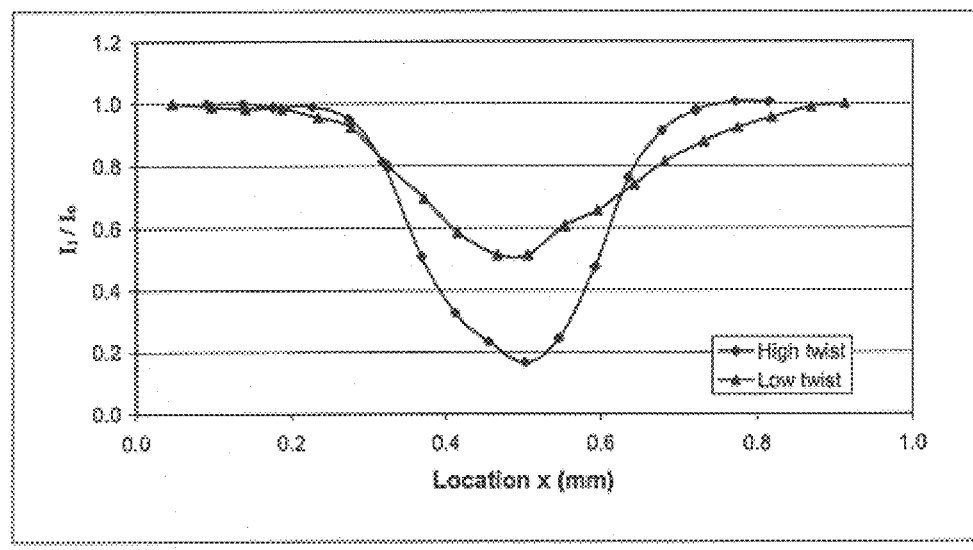
FIG. 4 is a graph showing relative x-ray absorption of yarns at different locations of a high twist and a low twist yarn.

Referring to the drawings, in FIG. 1 an X-ray tube 10 has a collimator 11 for directing X-rays in a path towards an X-ray detector 12. A pulse height analyzer 13 for determining attenuation of the X-rays supplies signals to a programmed computer 14. A vertically movable frame 15 supports a length of yarn 17 behind a narrow slit 16 and is arranged so the X-rays pass laterally through the yarn along a horizontal plane with a narrow beam. In use, the X-rays absorbed in each plane are monitored in turn by the analyzer 13. The yarn is then rotated to different rotational orientations and 'scanned' again by moving the frame to selected relative vertical positions representing a number of adjacent narrow planes.

In the set-up shown in FIG. 1, a Philips X'pert X-ray diffractometer is used for the scanning. A copper target of the X-ray tube is water-cooled and energised at 30 kV; the tube current is limited to 20 mA. A circular stainless steel tube and an aperture are used to collimate the X-ray beam to a size of about 2×5 mm². The yarn is mounted in the linear positioning frame 15 that is equipped with a digital micrometer of 1 μm reading resolution. The yarn is exposed to the collimated X-ray radiation at the rear of the 0.1 mm slit 16. A focusing optic system including a 0.1 mm aperture slit and a ½° field of view slit is used for the X-ray collection. A solid state detector 12 receives the X-ray radiation and the signals are fed to the pulse height analyser 13 and then recorded by the microcomputer 14. In order to deduct the background, the X-ray intensity is measured by scanning the detector for a small angle in each measurement.

The radiation wavelength is between 0.04 nm and 0.25 nm (corresponding to radiation energy of 30 KeV and 5 KeV). Preferred wavelengths are 0.083 nm and 0.15 nm (corresponding to radiation energy of 15 KeV and 8 KeV, respectively).

The computer 14 is programmed to determine the yarn density distribution relying on the principle of computed tomography (CT). As a cross-section of the yarn is scanned by a narrow x-ray beam, radiation intensity loss (attenuation) is recorded and processed by the computer to produce a two-dimensional image used for the computation of the yarn density distribution.

A physical model of CT is as follows. Let $f(r)$ be the X-ray attenuation function of the yarn at location r. The X-rays traversing a small distance dr at r suffer a relative intensity loss $dI/I$, with $dI/I=f(r) \cdot dr$. Let $I_o$ be the initial intensity of a X-ray beam L which is a straight line, and let $I_1$ be its intensity after having passed the yarn.

It follows that $$\frac{I_i}{I_o} = e^{-\int_L \mu(\%) f(r) dr}$$

The scanning process provides the line integral of the function f along each of lines L. From a number of these integrals, the function f has to be restructured. The transform which maps a function on R2 into the set of its line integrals is called the two-dimensional Radon transform. Thus the reconstruction problem of CT is the inversion of the Radon transform in R2. In practice the integrals can be obtained only for a finite number of lines L. In a parallel scanning geometry a set of equally spaced parallel lines are taken for a number of equally distributed directions. It requires the single source and the single detector which move in parallel and rotate during the scanning process. The real problem in CT is to reconstruct f from a finite number of its line integrals, and the reconstruction procedure has to be adapted to the scanning geometry.

In the described apparatus for practical purposes the yarn is assumed to have an axial symmetric packing density distribution.

The mathematical process of solving the following integral equation requires for a given density function m(x), to find out an unknown function $\phi(r)$, using:

$$\int_x^l \frac{r\varphi(r)}{\sqrt{r^2 - x^2}} dr = m(x) \quad (1)$$

The problem is solved by using the B-spline function. The B-spline function on equal-spaced knots is introduced by the following definition:

Let I=[a,b] be a given interval and $$\Delta := a = x_0 < x_1 < \ldots < x_{N-1} < x_N = b, \, x_i = a + i\frac{b-a}{N}, \, i = 0, 1, 2, \ldots, N$$

be a partition of I. Then the B-spline basis $\{B_i^n(x)\}$ of order n on $\Delta$ is defined as follows:

$$N_l(x) = \begin{cases} 1, & x \in [0, 1) \\ 0, & \text{otherwise} \end{cases}$$

$$N_n(x) = \frac{x}{n-1} N_{n-1}(x-1) + \frac{n-x}{n-1} N_{n-1}(x-1), n = 2, 3, \ldots$$

$$B_i^n(x) = N_n\left(\frac{N(x-a)}{b-a} - i + n - 1\right), i = 0, 1, \ldots N + n - 1$$

In the general practical case, the right term in (1) is known numerically and the measured data $\{(y_j, m_j)\}_{j=0}^M$ contains the error. Hence the measured data is calibrated or fitted by a smooth function. The scattered data via B-spline function is fitted or calculated. To preserve the trend of the measured data, the following constrained B-spline basis functions of order n=3 is used:

$$\left\{ A \frac{B_0^n(x)}{B_0^{n'}(a)}, B_1(x) - \frac{B_1^{n'}(a)}{B_0^{n'}(a)} B_0(x), B_2(x), \ldots, \right.$$

$$\left. B_{N-1}(x), B_N(x) - \frac{B_N^{n'}(b)}{B_{N+1}^{n'}(b)} B_{N+1}(x), B \frac{B_{N+1}^n(x)}{B_{N+1}^{n'}(b)} \right\}$$

Where $$A = C_1 \frac{m_1 - m_0}{y_1 - y_0}, B = C_2 \frac{m_M - m_{M-1}}{y_M - y_{M-1}}$$

and $C_1, C_2$ are calibration constants.

Let $$U_1(x) = B_1(x) - \frac{B_1^{n'}(a)}{B_0^{n'}(a)} B_0(x), U_i(x) = B_i(x), i = 2, 3, \ldots, N-1,$$

$$U_N = B_N(x) - \frac{B_N^{n'}(b)}{B_{N+1}^{n'}(b)} B_{N+1}(x)$$

$$g(x) = A \frac{B_0^n(x)}{B_0^{n'}(a)} + B \frac{B_{N+1}^n(x)}{B_{N+1}^{n'}(b)}$$

The aim of the following paragraph is to fit the given measured data $\{(y_j, m_j)\}_{j=0}^M$ by using a smooth spline function of the form $$s(x) = \sum_{i=1}^N c_i U_i(x) + g(x)$$

such that $$\sum_{j=0}^M (s(x_j) - m_j)^2 = \sum_{j=0}^M \left( \sum_{i=1}^N c_i U_i(x_j) + g(x_j) - m_j \right)^2 = \min$$

Which leads the following system of equation:

$$A \vec{C} = \vec{B}$$

where $A=(a_{kl})_{N \times N}$, $\vec{C}=(c_k)_{N \times 1}$, $\vec{B}=(b_k)_{N \times 1}$ and $$a_{kl} = \sum_{j=0}^M U_k(x_j) U_l(x_j), k, l = 1, 2, \ldots, N$$

$$b_k = \sum_{j=0}^M (m_j - g(x_j)) U_k(x_j)$$

For example, if measured data is

| $y_j$ | 0.000 | 0.1670 | 0.3330 | 0.5000 | 0.6670 | 0.8330 | 1.00000 |
|---|---|---|---|---|---|---|---|
| $m_j$ | 0.5385 | 0.4787 | 0.3550 | 0.2000 | 0.0703 | 0.0168 | 0.00015 |

Figure 5:
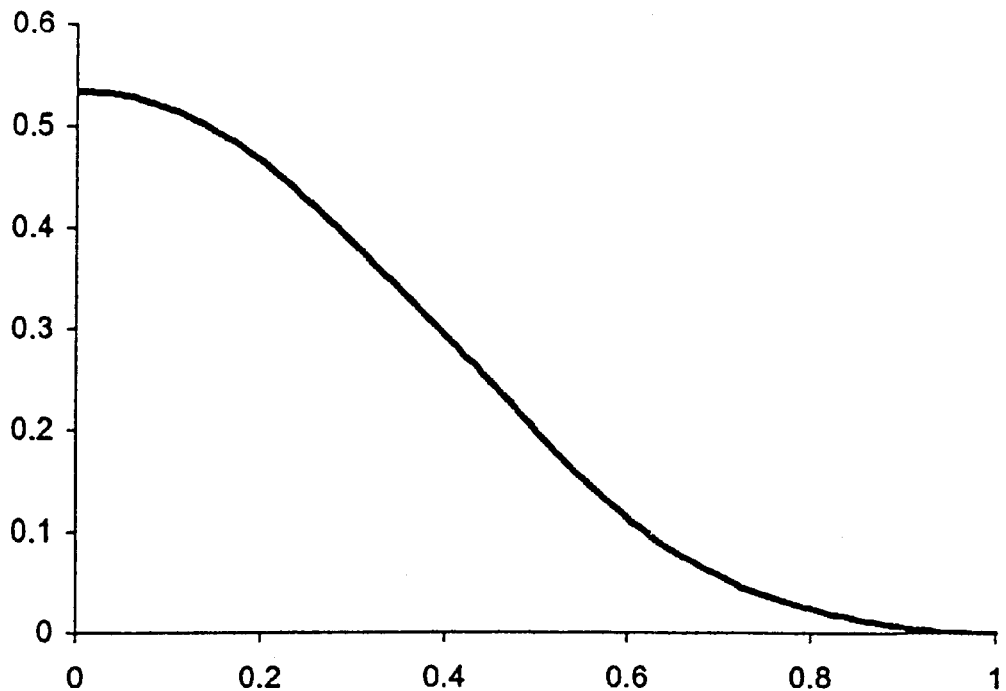
FIG. 5 is a graph showing a numerical solution of an equation for calculation yarn density distribution.

N=4, n=3 is taken, then the unknown coefficients are $c_1=-0.00358$, $c_2=-0.001$, $c_3=0.532899$ $c_4=0.320396$, $c_5=0.075187$, $c_6=-6.5E-05$ and the fitting smooth curve is shown in FIG. 5.

Using the fitted smooth function $s(x) \approx m(x)$, the equation (1) by B-spline function and by the following principle can be solved:

$$\sum \left( \left[ \int_{x_i}^1 \frac{r \sum_{j=0}^N C_j B_j(r)}{\sqrt{r^2 - x_i^2}} dr - s(x_i) \right] \right)^2 = \quad (2)$$

$$\sum \sum \left( \left[ C_j \int_{x_i}^1 \frac{r B_j(r)}{\sqrt{r^2 - x_i^2}} dr - s(x_i) \right] \right)^2 = \min.$$

To avoid singularity integral computation, the integrals in the above formula are computed numerically after part-integral, i.e., $$\int_{x_i}^1 \frac{r B_j(r)}{\sqrt{r^2 - x_i^2}} dr = \sqrt{1 - x_i^2} B_j(1) - \int_{x_i}^1 \sqrt{r^2 - x_i^2} B'_j(r) dr$$

The second integral in the right term of the above equation is computed by Simpson's integral formula. Denote by $$I(j; x) := \int_{x_i}^1 \frac{r B_j(r)}{\sqrt{r^2 - x_i^2}} dr.$$

It can be derived from (2)

$$A\vec{C} = \vec{B} \quad (3)$$

where $A=(a_{kl})_{N \times N}$, $\vec{C}=(C_k)_{N \times 1}$, $\vec{B}=(b_k)_{N \times 1}$ and $$a_{kl} = \sum_{j=0}^M I(k; x_j) I(l; x_j), k, l = 1, 2, \ldots, N$$

$$b_k = \sum_{j=0}^M s(x_j) I(k; x_j)$$

Figure 6:
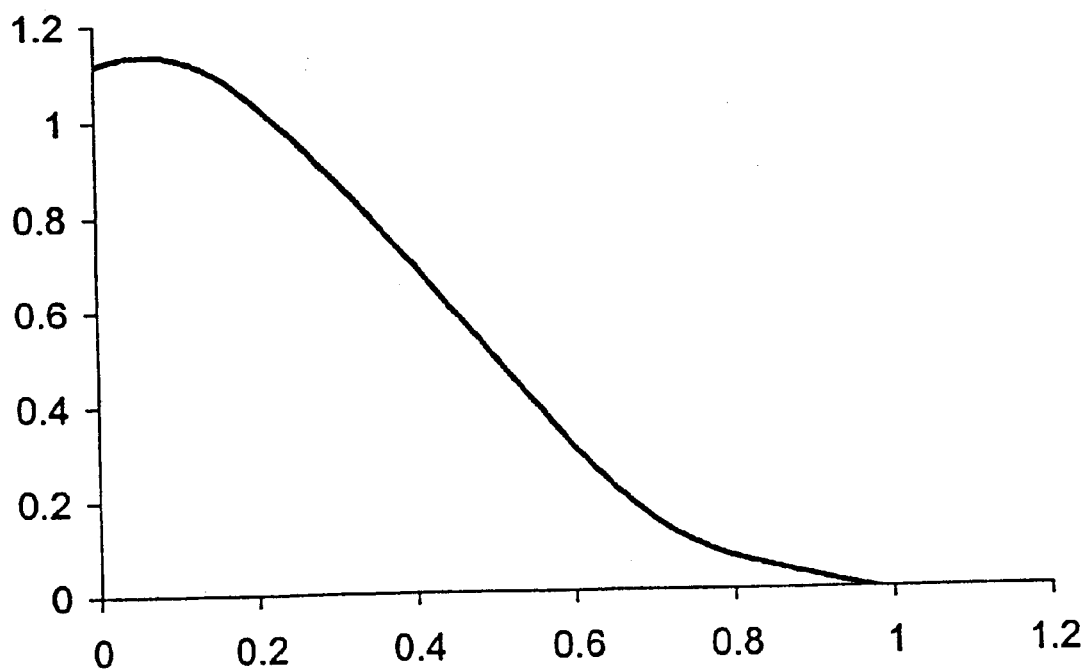
FIG. 6 is a graph showing a numerical solution of an equation for calculating yarn density distribution.

The numerical solution with N=5,M=30,n=3 of the problem for the measured data is shown in FIG. 6.

The density distribution measurements are therefore carried out in a non-destruction manner and relatively quickly. The apparatus may be configured and arranged to provide measurements that can be made alongside a spinning production line for use in quality control of the production process.

In the described embodiments, the X-ray detector measures radiation received in a single narrow plane as described, and the slit 16 is moved to direct the radiation along each plane in turn. Where a multiple sensor detector is used, effectively placed as a CCD array having one sensor for each adjacent narrow plane, the narrow slit 16 and movable frame are not required. Collimated X-rays are then directed generally at the yarn under test and attenuated radiation levels for each of the narrow planes measured individually and simultaneously. The yarn must still be rotationally orientated for subsequent (multiple) measuring.

We claim:

1. An apparatus for measuring lateral yarn density distribution of a yarn, the apparatus comprising:

a collimated source of radiation having a selected wavelength within the range of 0.04 nm to 0.25 nm corresponding to a radiation energy of 30 KeV to 5 KeV, a radiation detector for detecting the radiation, a moveable frame for mounting and rotating a length of yarn, in different rotational orientations, between the source and the radiation detector, and a computer executing an algorithm determining the density distribution of the length of yarn based on absorption of the radiation by the length of yarn in each of at least two different rotational orientations of the length of yarn.

2. The apparatus for measuring lateral yarn density distribution according to claim 1, wherein the radiation is constricted to a path extending in a plane of a section of the length of yarn, the radiation detector responds to radiation beyond the length of yarn along that path, and the moveable frame shifts the length of yarn, in steps, so that different planes in the path intersect the yarn.

3. The apparatus for measuring lateral yarn density distribution according to claim 1, wherein the radiation has a wavelength of 0.083 nm corresponding to a radiation energy of 15 KeV.

4. The apparatus for measuring the lateral yarn density distribution according to claim 1, wherein the radiation has a wavelength of 0.15 nm corresponding to a radiation energy of 8 KeV.

5. The apparatus for measuring lateral yarn density distribution according to claim 1, wherein the computer determines the yarn density using computed tomography.

6. The apparatus for measuring lateral yarn density distribution according to claim 1, including a narrow slit disposed between the source and the moveable frame and parallel to the length of yarn, wherein radiation passing through the slit is focused by the slit to intersect a narrow section of the length of yarn.

7. The apparatus for measuring lateral yarn density distribution according to claim 6, wherein the moveable frame moves in a direction perpendicular to the slit.

* * * * *